United States Patent
Hess et al.

(10) Patent No.: US 6,691,574 B2
(45) Date of Patent: Feb. 17, 2004

(54) METHOD AND DEVICE FOR MEASURING THE AMPLITUDE OF A FREELY OSCILLATING CAPILLARY OF A WIRE BONDER

(75) Inventors: Peter Hess, Walchwil (CH); Alexander Greber, Eich (CH); Markus Michler, Feldkirch (AT); Nicolino Onda, Bad Ragaz (CH)

(73) Assignee: ESEC Trading SA, Cham (CH)

( * ) Notice: Subject to any disclaimer, the term of this patent is extended or adjusted under 35 U.S.C. 154(b) by 0 days.

(21) Appl. No.: 10/373,212

(22) Filed: Feb. 24, 2003

(65) Prior Publication Data

US 2003/0159514 A1 Aug. 28, 2003

(30) Foreign Application Priority Data

Feb. 28, 2002 (CH) .............................................. 0369/02

(51) Int. Cl.$^7$ .............................. G01N 3/32; G01N 9/18; B23K 31/12
(52) U.S. Cl. .......................... 73/579; 73/655; 228/102; 228/103; 228/105
(58) Field of Search ........................ 73/579, 649, 1.79, 73/655; 228/102, 103, 105; 356/622, 621, 615; 702/94, 150

(56) References Cited

U.S. PATENT DOCUMENTS 5,199,630 A   4/1993   Felber et al. ................ 228/102

FOREIGN PATENT DOCUMENTS

| JP | 62 289733 | 12/1987 | |
|---|---|---|---|
| JP | 04 221722 | 8/1992 | |
| JP | 10 209199 | 8/1998 | |
| JP | 10209199 A | * 8/1998 | ........... H01L/21/60 |

* cited by examiner

Primary Examiner—Hezron Williams
Assistant Examiner—Tamiko Bellamy
(74) Attorney, Agent, or Firm—McCormick, Paulding & Huber LLP

(57) ABSTRACT

On measurement of a component $A_y$ of the amplitude of the oscillations of the tip of a capillary which is clamped to a horn to which ultrasonics can be applied from an ultrasonic transducer, whereby measurement is based on the shading of a light beam by the capillary and whereby the intensity of the light beam is measured by means of an opto-receiver, the capillary is placed at one side of the light beam without it shading the light beam and ultrasonics is applied to it. The capillary is then moved in steps through the light beam whereby, for each of the i=1 to n steps, the direct voltage portion $U_{DC}(y_i)$ and the alternating voltage portion $U_{AC}(y_i)$ of the output signal of the opto-receiver are determined as well as a co-ordinate $y_i$ whereby the co-ordinate $y_i$ designates the position of the capillary in relation to a co-ordinate axis y running perpendicularly to the light beam. The amplitude $A_y$ is then calculated from the values measured.

4 Claims, 4 Drawing Sheets

Figure 1:
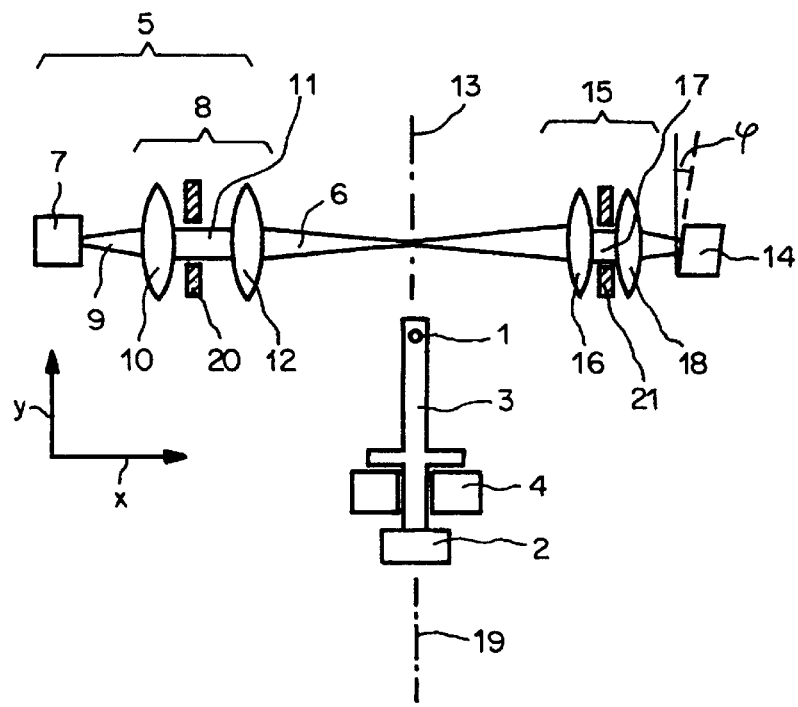

METHOD AND DEVICE FOR MEASURING THE AMPLITUDE OF A FREELY OSCILLATING CAPILLARY OF A WIRE BONDER

PRIORITY CLAIM

The present application claims priority under 35 U.S.C § 119 based upon Swiss Patent Application No. 2002 0369/02 filed on Feb. 28, 2002 which is incorporated herein by reference.

FIELD OF THE INVENTION

The invention concerns a method and a device for measuring the amplitude of a freely oscillating capillary of a Wire Bonder.

BACKGROUND OF THE INVENTION

A Wire Bonder is a machine with which semiconductor chips are wired after mounting on a substrate. The Wire Bonder has a capillary which is clamped to the tip of a horn. The capillary serves to secure the wire to a connection point on the semiconductor chip and to a connection point on the substrate as well as to guide the wire between the two connection points. On producing the wire connection between the connection point on the semiconductor chip and the connection point on the substrate, the end of the wire protruding out of the capillary is first melted into a ball. Afterwards, the wire ball is secured to the connection point on the semiconductor chip by means of pressure and ultrasonics. In doing so, ultrasonics is applied to the horn from an ultrasonic transducer. This process is called ball bonding. The wire is then pulled through to the required length, formed into a wire loop and welded to the connection point on the substrate. This last part of the process is called wedge bonding. After securing the wire to the connection point on the substrate, the wire is torn off and the next bonding cycle can begin.

A method and a device for measuring the amplitude of the freely oscillating capillary are known from the European patent EP 498 936 B1. The measured value is used for calibrating the ultrasonic transducer. The measurement of the oscillation amplitude of the capillary is done by means of a light barrier.

A method and a device for measuring the amplitude of the freely oscillating capillary with which a laser beam is used for the light barrier are known from the Japanese patent 10-209 199.

Experiments have shown that measurement with the known technique does not provide reproducible results when the amplitude of the tip of the freely oscillating capillary is to be measured.

SUMMARY OF THE INVENTION

The object of the invention is to develop a method and a device for measuring the amplitude of the tip of a freely oscillating capillary.

The method in accordance with the invention is based on the shading of a light beam by means of the capillary whereby the oscillations of the capillary modulate the intensity of the let-through light beam. The intensity of the let-through light beam is measured by means of an opto-receiver. Generally, the direction of oscillation of the capillary in the plane is not known. However it is generally the case that the oscillations of the capillary mainly run in the direction of the longitudinal axis of the horn. With the measuring principle of the shading of a light beam, only that component of the amplitude of the oscillations of the capillary can be measured which runs perpendicularly to the direction of the light beam.

Unfortunately there are numerous undesirable effects such as, for example, contamination of the capillary, diffraction on the capillary, gradual surface variations of the capillary, asymmetries of the light beam, etc, which hamper a reproducible measurement when no special measures are taken. The invention consists in carrying out a number of measurements and averaging the measured values acquired. In a first step, the capillary is adjusted in relation to the light beam. Afterwards, the component $A_y$ of the oscillations of the capillary which runs perpendicularly to the direction of the light beam is determined according to the following steps,:

a) Placing the capillary at one side of the light beam without it shading the light beam and applying ultrasonics to the horn;

b) Moving the capillary in a given number of n steps along a predetermined direction w where "w" is not necessarily perpendicular to the light beam into the light beam or completely through the light beam until it is located at the other side of the light beam whereby, with each of the i=1 to n steps, the direct voltage portion $U_{DC}(y_i)$ and the alternating voltage portion $U_{AC}(y_i)$ of the output signal $U_P(y_i)$ of the opto-receiver are determined as well as a co-ordinate $y_i$ whereby the co-ordinate $y_i$ designates the position of the capillary in relation to a co-ordinate axis y running perpendicularly to the light beam and whereby the component $A_y$ to be measured runs in the direction of the co-ordinate axis y;

c) Calculation of sensitivity values $S_i(y_i)$ as a derivation of the direct voltage portion $U_{DC}(y_i)$ with respect to the co-ordinate axis y as $$S_i(y_i) = \frac{dU_{DC}(y_i)}{dy};$$

d) Selection of at least four measurement points and, for each of these at least four measurement points, calculation of a value $A_{y,i}$ as $$A_{y,i} = \frac{U_{AC}(y_i)}{S_i(y_i)};$$

e) Calculation of the component $A_y$ as an average of the values $A_{y,i}$.

Advantageously, the calculation of the component $A_y$ is done by the use of statistical methods. It is of particular advantage to smooth the sensitivity values $S_i(y_i)$ calculated in step c, for example by averaging over neighbouring measuring points. It is also of advantage to smooth the measured values $U_{DC}(y_i)$ and $U_{AC}(y_i)$. It is of further advantage to take into consideration not only four measurements but as many measurements as possible. A possible criterion for selection of the measurements is, for example, that the sensitivity $S_i$ exceeds a predetermined minimum value.

BRIEF DESCRIPTION OF THE DRAWING FIGURES

Figure 11:
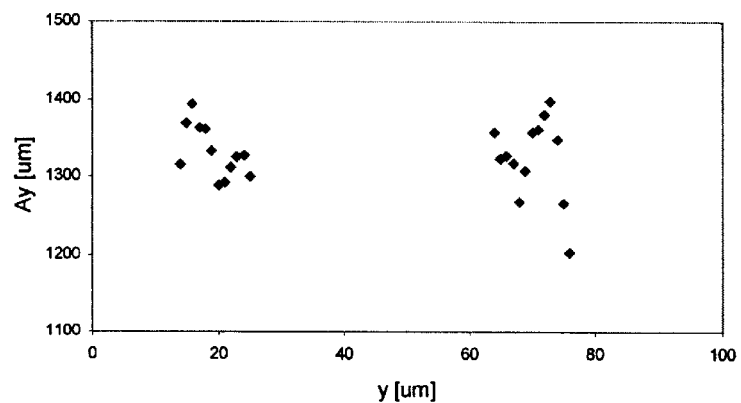
Figure 12:
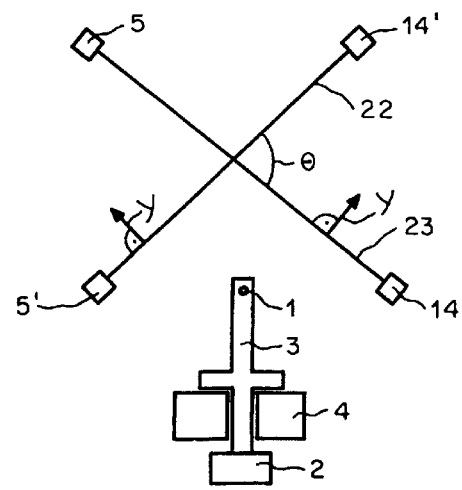
Figure 13:
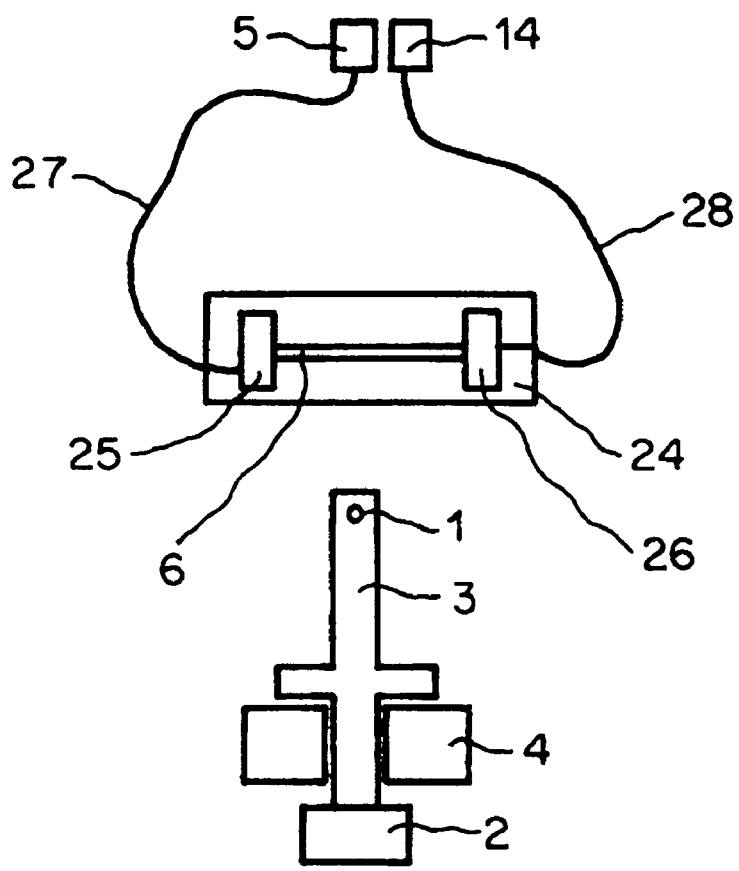

The accompanying drawings, which are incorporated into and constitute a part of this specification, illustrate one or more embodiments of the present invention and, together with the detailed description, serve to explain the principles and implementations of the invention. The figures are not to scale. In the drawings:

FIG. 1 shows a measuring device for measurement of the amplitude of the tip of a freely oscillating capillary based on the shading of a light beam, FIGS. 2–6 show different positions of the tip of the capillary in relation to the light beam, FIGS. 7–11 show different diagrams, and FIGS. 12, 13 show further measuring devices.

DETAILED DESCRIPTION OF THE PREFERRED EMBODIMENTS

FIG. 1 shows a plan view of a capillary 1 which is clamped onto the tip of a horn 3 to which ultrasonics can be applied from an ultrasonic transducer 2 and a measuring device for measuring the amplitude of the oscillations of the tip of the capillary 1. The co-ordinates of a Cartesian system of co-ordinates are marked with x, y and z whereby the z co-ordinate runs vertically to the plane of the drawing. The horn 3 is secured to the bondhead 4 of a Wire Bonder. The bondhead 4 enables movement of the tip of the capillary 1 in all three co-ordinate directions. The measuring device comprises a light source 5 for the production of a light beam 6 with a diameter well defined in a working area of the device. The light source preferably consists of a laser diode 7 and a first optical assembly 8 which transforms the cone of light 9 emitted by the laser diode 7 into the light beam 6. In the example, the first optical assembly 8 consists of a first lens 10 which concentrates the cone of light 9 emitted by the laser diode 7 into a beam of parallel light 11, and a second lens 12 which re-focuses the light so that the diameter of the light beam 6 is minimal in a focal plane 13 of the second lens 12. At the same time, this focal plane 13 is the measuring plane for measurement of the oscillation amplitude of the capillary 1. Furthermore, the device includes an opto-receiver 14 and a second optical assembly 15 in order to image the light beam 6 onto the opto-receiver 14. The second optical assembly 15 consists of a first lens 16 which concentrates the light beam 6 which diverges again after the measuring plane into a beam of parallel light 17, and a second lens 18 which focuses the beam of parallel light 17 onto the opto-receiver 14. The diameter of the tip of the capillary 1 amounts to around 50 $\mu$m to 150 $\mu$m. The effective diameter of the light beam 6 in the measuring plane is smaller than the diameter of the capillary 1 at the point to be measured. In the example, the diameter of the light beam 6 amounts to around 21 $\mu$m.

As can be seen from FIG. 1, the light beam 6 runs in x direction. The longitudinal axis 19 of the horn 3 runs in y direction. To measure the amplitude of the oscillations of the tip of the capillary 1, the tip of the capillary 1 is positioned in the focal plane 13 of the lens 12 in such a way that it shades a part of the light beam 6. When the ultrasonic transducer 2 is switched on, the tip of the capillary 1 oscillates in the xy plane. The y component $A_y$ of these oscillations causes a change in the shading of the light beam 6 which is detected by the opto-receiver 14 while the x component $A_x$ of these oscillations does not change the shading.

The measuring device distinguishes itself by means of two particular features. On the one hand, the opto-receiver 14 is inclined by a predetermined angle $\phi$ in relation to the light beam 6 so that the portion of the light beam 6 reflected at the surface of the opto-receiver 14 does not reflect back onto the capillary or even as far as the laser diode 7 but "leaves" the measuring device "without interfering". A 1–2° inclination of the angle $\phi$ already suffices. The light beam 6 therefore impinges on the opto-receiver 14 at an angle differing from 90°. On the other hand, each of the two optical assemblies 8 and 15 preferably includes a shield 20 or 21 in order to intercept stray light.

Figure 2:
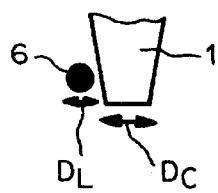
Figure 3:
Figure 4:
Figure 5:
Figure 6:

FIG. 2 shows the tip of the capillary 1 and the light beam 6. The diameter $D_L$ of the light beam 6 is smaller than the diameter $D_C$ of the tip of the capillary 1.

In order to be able to reliably measure the amplitude of the oscillations of the tip of the capillary 1, in the first part of the method, the z height of the capillary 1 must be adjusted in relation to the light beam 6. This is done in accordance with the following steps:

1. The capillary 1 is placed at one side of the light beam so that it does not shade the light beam. Furthermore, it is lowered sufficiently in z direction so that, in the next step, it will completely cover the light beam.
2. The capillary 1 is moved step-by-step through the light beam in y direction until it is located at the other side of the light beam. Afterwards, a position $y_0$ is determined from the signal delivered by the opto-receiver at which the light beam impinges roughly in the centre of the capillary. This position $y_0$ is presented in FIG. 3.
3. The capillary 1 is brought into the position $y_0$ and then raised in z direction until the output signal from the opto-receiver reaches a predetermined value which typically makes around 5% of the signal when the capillary does not shade the light beam. This position, designated in the following as $z_0$, is presented in FIG. 4.

In a second part of the method, the y component $A_y$ of the amplitude A of the oscillations of the tip of the capillary 1 is now determined in accordance with the following steps:

a) The capillary 1 is brought into position $z_0$ and placed in y direction at one side of the light beam 6 so that it does not shade the light beam 6. Ultrasonics is applied to the horn 3 by the ultrasonic transducer 2.
b) The capillary 1 is now moved in a number of n steps through the light beam 6 in y direction until it is located at the other side of the light beam 6. The output signal $U_P$ of the opto-receiver 14 contains a direct voltage portion $U_{DC}$ and an alternating voltage portion $U_{AC}$:

$$U_P = U_{DC} + U_{AC}. \quad (1)$$

The direct voltage portion $U_{DC}$ comes from that part of the light beam 6 which is not covered by the capillary 1. The alternating voltage portion $U_{AC}$ comes from that part of the light beam 6 which is modulated by the tip of the capillary 1 as a result of its oscillations. At each of the i=1 to n steps, the portions $U_{DC}(y_i)$ and $U_{AC}(y_i)$ of the output signal $U_P(y_i)$ of the opto-receiver 14 as well as the corresponding y co-ordinate $y_i$ are determined and saved.

The distance between two neighbouring co-ordinates $y_i$ and $y_{i+1}$ amounts typically to 1 $\mu$m.

The alternating voltage portion $U_{AC}$ is linked to the y component $A_y$ of the oscillations of the tip of the capillary 1 as follows:

$$U_{AC} = S(y) * A_y = \frac{dU_{DC}(y)}{dy} * A_y, \quad (2)$$

whereby the sensitivity S(y) is given by the derivation of the direct voltage portion $U_{DC}$ with respect to the co-ordinate y.

c) Now, for each measuring step i, the derivation $$\frac{dU_{DC}(y_i)}{dy}$$

is calculated from the measured values $U_{DC}(y_i)$ and saved as the sensitivity $S_i(y_i)$:

$$S_i(y_i) = \frac{dU_{DC}(y_i)}{dy}. \quad (3)$$

In accordance with equation (3), an amplitude $A_{y,i}$ can now be calculated for each measuring point i as $$A_{y,i} = \frac{U_{AC}(y_i)}{S_i(y_i)}. \quad (4)$$

d) By means of averaging, an average for the y component $A_y$ of the amplitude A of the oscillations of the tip of the capillary 1 is calculated from the values $A_{y,i}$ in accordance with equation (4).

For calculation of the average value of the y component $A_y$ in accordance with the above method steps c and d, it is preferable to consider not all but only those measuring points at which the sensitivity S exceeds a minimum value. This is the case when the capillary 1 moves into the light beam 6 and when it moves out again, therefore when the capillary 1 only partially covers the light beam 6 as is presented in FIGS. 5 and 6. Therefore, only those measuring points are selected which, from a physical aspect, actually provide a usable measured value. In the area where the capillary 1 almost fully shades the light beam 6, its oscillations contribute nothing to the measurement signal. Furthermore, it is of advantage to apply the usual methods used in statistics. It is particularly advantageous to smooth the calculated sensitivities $S_i(y_i)$. Smoothing can be done in that the average is also formed over three neighbouring measured values for example or by means of fitting to a predetermined function. It is also advantageous to smooth the measured values $U_{DC}(y_i)$ and $U_{AC}(y_i)$ and to use the corresponding smoothed values in the equations (3) and/or (4). It is also advantageous to omit any freak values.

Figure 7:
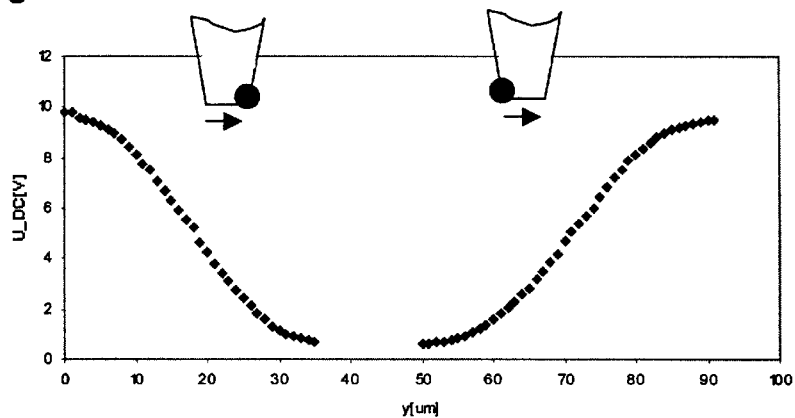
Figure 8:
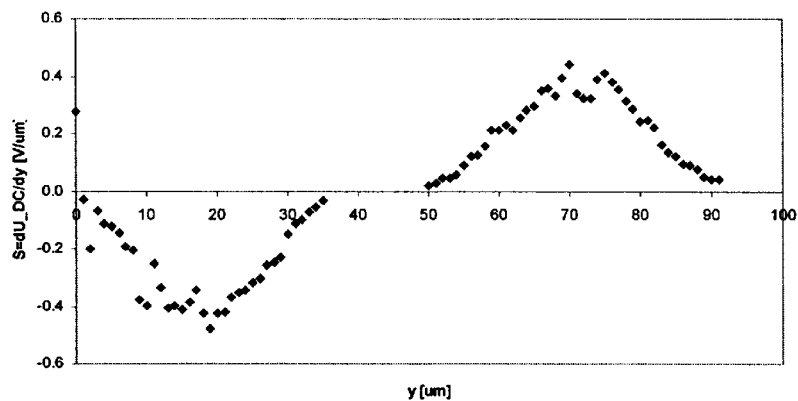
Figure 9:
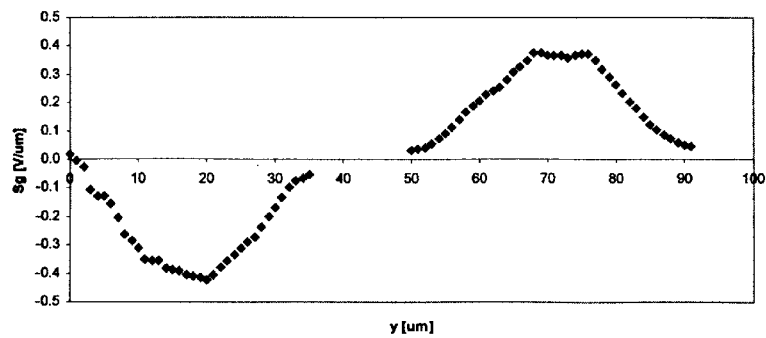
Figure 10:
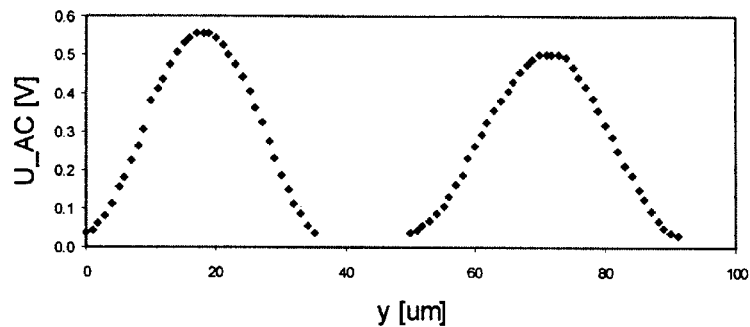

FIGS. 7 to 11 show the direct voltage portion $U_{DC}(y_i)$, the sensitivity $S_i(y_i)$ calculated from it and smoothed values $S_g(y_i)$ for the sensitivity $S_i(y_i)$, the alternating voltage portion $U_{AC}(y_i)$ and the amplitudes $A_{y,i}$ calculated from the alternating voltage portion $U_{AC}(y_i)$ and the smoothed sensitivity $S_g(y_i)$ as a function of the y co-ordinate $y_i$. In FIG. 7, the position of the capillary 1 relative to the light beam 6 is also shown schematically whereby an arrow indicates the movement direction of the capillary 1. In FIG. 11, only those amplitudes $A_{y,i}$ are calculated and presented where the corresponding sensitivity $S_i(y_i)$ exceeds a predetermined minimum value. The average of these amplitudes $A_{y,i}$ was determined in step d in order to acquire a single value for the component $A_y$ of the amplitude A of the oscillations of the tip of the capillary 1. In the example, for the component $A_y$ the value $A_{y,in}$=1.331 μm±0.033 μm results from the measuring points when the capillary 1 moves into the light beam 6 and the value $A_{y,out}$=1.334 μm±0.040 μm from the measuring points when the capillary 1 moves out of the light beam 6. The values $A_{y,in}$ and $A_{y,out}$ are therefore almost equal and, altogether, for the component $A_y$ one gets the value $A_y$=1.332 μm±0.037 μm.

It is in fact meaningful to move the capillary 1 completely through the light beam 6 and, in doing so, to record as many measuring points as possible as the accuracy is increased with every measuring point. It is however also possible to move the capillary 1 only partially into the light beam 6.

FIG. 12 shows a measuring device with two light beams 22 and 23 running at a predetermined angle θ to each other which are produced by the light sources 5 and 5' and the intensity of which is measured by opto-receivers 14 and 14'. With this measuring device, two components $A_1$ and $A_2$ of the amplitude A of the oscillations of the capillary 1 can be measured. The component A1 designates that component of the amplitude A which runs in the xy plane and perpendicularly to the direction of the first light beam 22, the component $A_2$ designates that component of the amplitude A which runs in the xy plane and perpendicularly to the light beam 23. Each of the components $A_1$ and $A_2$ can be determined in accordance with the method described above and the amplitude A can then be calculated with conventional mathematics on incorporation of the actual geometry. With the example explained based on FIG. 1, the movement axis of the capillary 1 runs perpendicularly to the direction of the light beam 6. In the example according to FIG. 12, the movement of the capillary 1 can be selected perpendicularly to the direction of the respective light beam 22 or 23 for measurement of the components $A_1$ and $A_2$. The movement of the capillary 1 can however also take place along a predetermined direction w where w is not perpendicular to the light beam. In this case, the co-ordinate $y_i$ designates the component of the movement perpendicular to the direction of the respective light beam 22 or 23. In each case therefore, the co-ordinate $y_i$ designates the position of the capillary 1 in relation to a direction running perpendicularly to the direction of the corresponding light beam 22 or 23. The directions y are presented for both light beams 22 and 23.

The measuring devices according to FIGS. 1 and 12 can be permanently installed on the Wire Bonder so that the oscillation amplitude of the capillary can be measured at any time.

FIG. 13 shows a measuring device which is suitable as a portable unit for use on different Wire Bonders. The measuring device comprises a platform 24 on which two so-called snap-on focusers 25 and 26 are securely arranged. A first fibre 27 connects the light source 5 with the first snap-on focuser 25, a second fibre 28 connects the second snap-on focuser 26 with the opto-receiver 14. The first snap-on focuser 25 has the task of transforming the light guided through the first fibre 27 into a light beam 6 which is focussed on a measuring plane. The second snap-on focuser 26 has the task of injecting the light of the light beam 6 let through by the capillary 1 into the second fibre 28.

The ultrasonic transducer 2 (FIG. 1, FIG. 12 and FIG. 13) of the Wire Bonder is controlled by a parameter P. The parameter P is, for example, the current which flows through the ultrasonic transducer or the voltage which is applied to the ultrasonic transducer. As a rule, the relationship between the parameter P and the amplitude A is linear:

$$A = \gamma * P \quad (5)$$

The measurement of the component $A_y$ of the amplitude A of the oscillations of the tip of the capillary 1, or the measurement of the amplitude A therefore enables determining of the constant γ. In production operation of the Wire Bonder, the constant γ can then be re-determined after each capillary change by means of a measurement and be taken into consideration for production.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims and their equivalents.

What is claimed is:

1. A method for measuring a component $A_y$ of an amplitude of oscillations of a tip of a capillary of a wire bonder which is clamped to a horn to which ultrasonics can be applied from an ultrasonic transducer, whereby measurement is based on a shading of a light beam by the capillary and whereby an intensity of the light beam is measured by an opto-receiver, comprising the following steps:

Placing the capillary at one side of the light beam without the capillary shading the light beam and applying ultrasonics to the horn;

Moving the capillary in a predetermined number of n steps into the light beam or completely through the light beam along a predetermined direction, whereby, at each of the i=1 to n steps, a direct voltage portion $U_{DC}(y_i)$ and an alternating voltage portion $U_{AC}(y_i)$ of an output signal of the opto-receiver as well as a co-ordinate $y_i$ are determined, whereby the co-ordinate $y_i$ designates a position of the capillary in relation to a co-ordinate axis y running perpendicularly to the light beam and whereby the component $A_y$ to be measured runs in direction of the co-ordinate axis y;

Calculating sensitivity values $S_i(y_i)$ as a derivation of the direct voltage portion $U_{DC}(y_i)$ with respect to the co-ordinate axis y as $$S_i(y_i) = \frac{dU_{DC}(y_i)}{dy};$$

Selecting at least four measurement points and, for each of these at least four measurement points, calculating a value $A_{y,i}$ as $$A_{y,i} = \frac{U_{AC}(y_i)}{S_i(y_i)};$$

and

Calculating the component $A_y$ as an average from the values $A_{y,i}$.

2. The method according to claim 1, wherein the sensitivity values $S_i(y_i)$ are smoothed.

3. The method according to claim 1, wherein two different components of the amplitude of the oscillations of the capillary are determined.

4. The method according to claim 2, wherein two different components of the amplitude of the oscillations of the capillary are determined.

* * * * *